United States Patent [19]
Hopf

[11] Patent Number: 5,702,395
[45] Date of Patent: Dec. 30, 1997

[54] SPINE OSTEOSYNTHESIS INSTRUMENTATION FOR AN ANTERIOR APPROACH

[75] Inventor: Christoph Hopf, Mainz, Germany

[73] Assignee: Sofamor S.N.C., Rangdu Fliers, France

[21] Appl. No.: 433,500

[22] PCT Filed: Nov. 10, 1993

[86] PCT No.: PCT/US93/10908

§ 371 Date: May 10, 1995

§ 102(e) Date: May 10, 1995

[87] PCT Pub. No.: WO94/10927

PCT Pub. Date: May 26, 1994

[30] Foreign Application Priority Data

Nov. 10, 1992 [FR] France ................... 92 13538

[51] Int. Cl.[6] .............................. A61B 17/70
[52] U.S. Cl. .............................. 606/61; 606/73
[58] Field of Search ................... 606/61, 53, 60, 606/69, 70, 71, 72, 73

[56] References Cited

U.S. PATENT DOCUMENTS

| | | | |
|---|---|---|---|
| 4,289,123 | 9/1981 | Dunn | 128/84 |
| 5,030,220 | 7/1991 | Howland | 606/61 |
| 5,074,864 | 12/1991 | Cozad et al. | 606/54 |
| 5,108,395 | 4/1992 | Laurain | 606/61 |
| 5,147,360 | 9/1992 | Dubousset | 606/61 |
| 5,152,303 | 10/1992 | Allen | 606/60 |
| 5,312,405 | 5/1994 | Korotko et al. | 606/61 |
| 5,330,473 | 7/1994 | Howland | 606/61 |

Primary Examiner—Michael Buiz
Assistant Examiner—David O. Reip
Attorney, Agent, or Firm—Woodard, Emhardt, Naughton, Moriarty & McNett

[57] ABSTRACT

The instrumentation comprises at least two blocks (1) adapted to transversely interconnect two rigid rods (2, 3) axially slidable in these blocks which are provided with bone anchorage screws (7, 8) suitable oriented and slides (4, 5) which are slidable in longitudinal recesses (6, 7) receiving the respective rods (2, 3) which may be in this way clamped by the slides after the latter have been completely closed. Each block (1) has in the transverse direction from the anterior part to the posterior part a curved general shape corresponding to the antero-lateral anatomy of the vertebral bodies, the interior surface being consequently concave while the exterior surface is convex. The instrumentation obtained by the assembly of two blocks (1), anchorage screws and stiffening rods (2, 3) forms a very stable rectangular structure restoring the axial continuity of the vertebral column, avoiding correction losses and facilitating the consolidation of the bone graft.

40 Claims, 7 Drawing Sheets

SPINE OSTEOSYNTHESIS INSTRUMENTATION FOR AN ANTERIOR APPROACH

The present invention relates to a spinal osteosynthesis instrumentation for an anterior approach.

In the field of spinal instrumentation, instrumentation for a posterior approach has been widely explored and still remains an interesting solution in many pathological cases.

However, this technique has the drawback of not permitting direct access to the vertebral bodies, which often limits the use thereof and encourages an exploration of another approach, such as the anterior approach.

Although it is much more delicate and complex than the instrumentation for a posterior approach, the instrumentation for an anterior approach opens up a wider field of investigation. It is becoming necessary to investigate this field despite the fact that this approach requires considerable technical means and environment in the hospital and a specific training of very highly specialized orthopaedic surgery practitioners.

Depending on the vertebral level to be reached, several techniques of access by an anterior approach are at present practiced. They are:
Transpleural thoracotomy in the thoracic region,
Thoraco-phrenolumbotomy in the thoracolumbar region,
Lumbotomy in the lumbar region.

For each of these techniques, the approach on the left side of the vertebral column is preferred despite the proximity of the aorta, owing to the presence on the right side of the vena cava which is more fragile and less easy to move than the aorta.

However, the extension of the large vessels along the vertebral bodies has repercussions on the mounting of an instrumentation.

The technique by the anterior approach of the dorsolumbar spine is employed:
either for correcting a scoliosis and maintaining its correction,
or for treating a kyphosis with a large radius of curvature or an angular kyphosis.

Some surgeons are afraid of this technique; however, it is acknowledged to favour the treatment of certain pathologies. It is even indispensable in certain cases.

Whatever be the surgical schools of thought formed around spinal instrumentation, all surgeons acknowledge the following advantages of this technique:
Obtainment of an improved derotation of the vertical column and an improved correction of dorso-lumbar scolioses;
Obtainment of an improved instrumental stabilization, an improved correction of cyphoses, and an improved nerve decompression;
Direct viewing of the vertebral part to be treated in the anterior region and in the median region of the column;
Use of a relatively short length of instrumentation and fusion;
Higher fusion rate, approaching a value on the order of 95%;
Reduced medullary risks owing to a direct approach to the marrow and the necessity of distraction by a posterior action.

These advantages are of course not exhaustive and there could also be mentioned: an improved decompression, the non-destruction and therefore the preservation of the posterior stabilizing elements such as the muscles and ligaments, etc.

Resulting from the interest of the development of instrumentation for an anterior approach, many technical propositions have been made which may be resumed as follows:

Devices employing plates or the like fixed at the ends of the latter to the vertebrae located on each side of the vertebral region to be treated;

Devices employing rods, usually two rods, stiffened therebetween by transverse bars to which they are fixed thus forming a rectangular frame.

Each of the proposed structures has its specific advantages but also its drawbacks, with the result that the considered instrumentation is not or relatively rarely employed.

Two known examples may be mentioned:
French patent 2651992 (8912187, inventor J. M. LAURAIN) proposes the use of a rigid plate. Such a device corresponds to the specific requirements of fractures and tumors and of the degenerative field, but is hardly suitable for vertebral deviations.
French patent 2653413 (9001970, inventor J. DUBOUSSET) proposes the use of two metal rods fixed along the vertebral column and interconnected transversely by two rigid bars, which imparts to the instrumentation a rectangular frame arrangement.

This solution is well suited to the problems of spinal deviations, but does not satisfy all the technological and surgical requirements.

In particular, the large number of parts making up the instrumentation implies a relatively long operating time and consequently this instrumentation, although effective, is costly, which hinders its extension and marketing. In brief, the instrumentation for an anterior approach is very delicate and represents for the surgeons a high risk that technological innovation must attempt to reduce as far as possible.

Therefore, an object of the invention is to provide an instrumentation which permits overcoming these shortcomings and therefore treating, indifferently in a completely satisfactory manner, fractures and tumours as well as spinal deviations.

The invention provides an instrumentation which comprises two rigid rods parallel to each other or contained in parallel planes, at least two blocks adapted to transversely interconnect said rods in such manner that they are axially slidable and revolvable about themselves in said blocks, said blocks being provided with means for clamping the rods against rotation and translation, and bone anchorage elements for said blocks.

Two blocks and the two associated rods thus make up a rectangular frame affording all of the required stability for restoring the axial continuity of the vertebral column, avoiding correction losses, and facilitating the consolidation of the bone graft.

According to an embodiment of the invention, each block has in a transverse direction, from an anterior part toward a posterior part of the vertebral bodies, a generally curved shape corresponding to the antero-lateral anatomy of the vertebral bodies, the interior surface intended to be applied on a vertebral body being therefore concave while the exterior surface is convex.

According to other features:
The concave surface of the anterior part facing toward the vertebral body has a radius of curvature less than that of the exterior convex surface of the block;
Formed in each block are two parallel longitudinal recesses for receiving a respective rod, and a slide for clamping the rod, said slide being longitudinally slidable in the corresponding recess and becoming clamped on the rod at the end of its travel;
Each slide is provided with inclined lateral flanges adapted to be engaged in complementary lateral grooves in the recess, and said flanges cooperate with inclined clamping ramps provided in said grooves, or, inversely, the flanges are inclined and cooperate with clamping ramps provided in said recesses;

In a possible embodiment of the invention, the block is bent so as to have a substantially S-shaped cross-section the two halves of which constitute the anterior and posterior parts, the anterior part having a thickness less than that of the posterior part and being capable of being inserted in a recess provided for this purpose in the vertebral body.

Further features and advantages of the invention will be apparent from the following description with reference to the accompanying drawings which show several embodiments of the invention by way of non-limitative examples.

The spinal osteosynthesis instrumentation for an anterior approach shown in FIGS. 1 to 7 comprises at least two blocks 1 adapted to transversely interconnect two rigid rods 2, 3 which are parallel to each other and axially slidable in said blocks. The instrumentation is shown in the vertical position viewed on the left side of the spine. The blocks 1 are provided with means for clamping the rods 2, 3 against rotation and translation and comprising essentially, for each block 1, 2, two slides 4, 5 movable in translation in a direction parallel to the rods 2, 3 in corresponding recesses 6, 7 provided in the blocks 1, 2.

Figures 1, 2, 3:
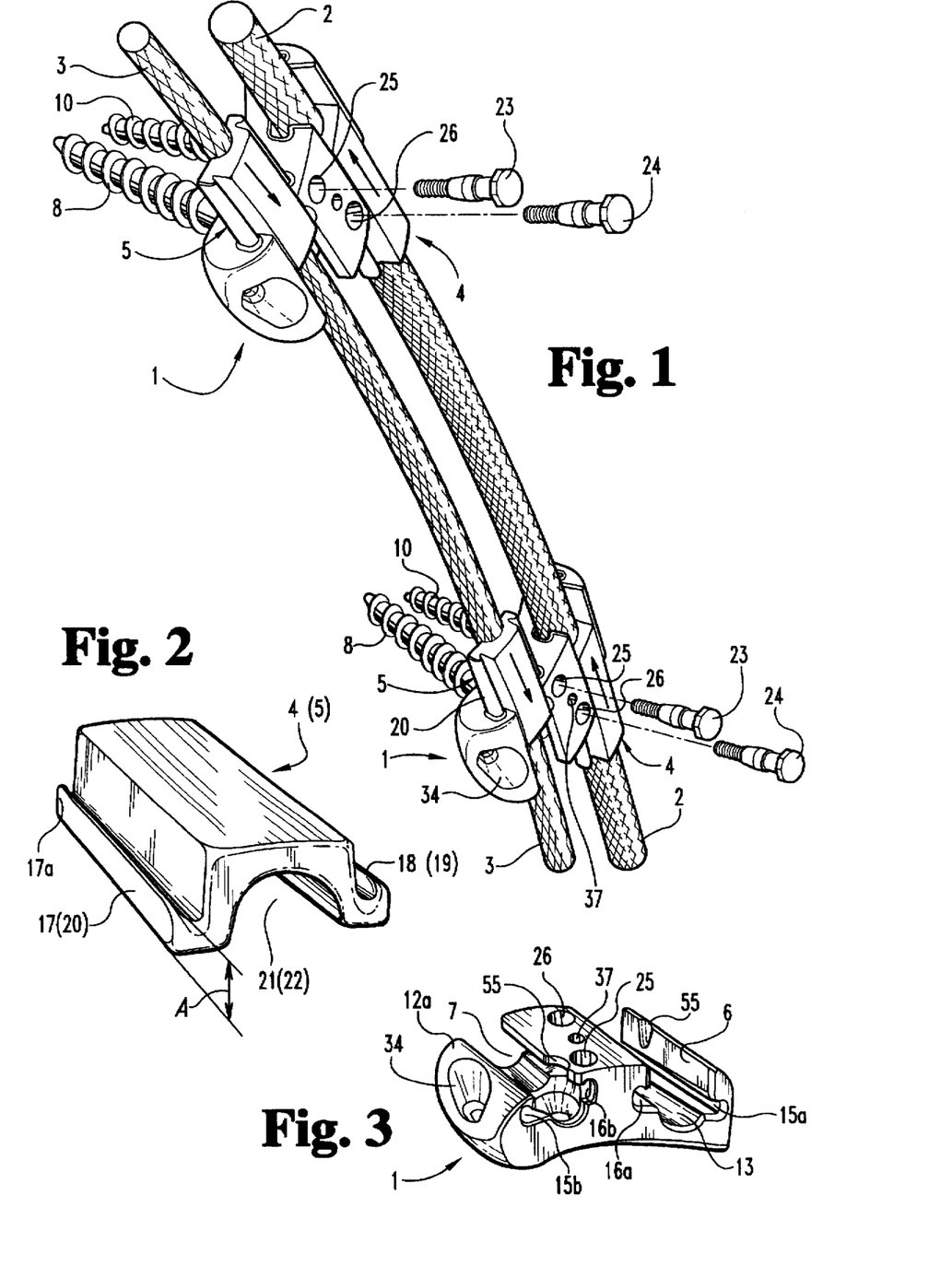
FIG. 1 is a partly exploded perspective view of a first embodiment of the spinal osteosynthesis instrumentation for an anterior approach according to the invention.
FIG. 2 is a perspective view to a larger scale relative to FIG. 1 of a slide for closing the recess of the block shown in FIG. 1.
FIG. 3 is a perspective view of one of the blocks of the instrumentation shown in FIG. 1 to a smaller scale than in FIG. 2.

Each block 1, 2 is also provided with a pair of bone anchorage screws 8, 10 which may be placed in position by inserting them in corresponding bores 9, 11 provided in the bottom of the recesses 6 and 7. The bores 9, 11, and therefore the screws 8, 10, have suitable inclinations so that the two screws converge at a suitable angle, preferably on the order of 25°.

Advantageously, the screws 8, 10 have a conical head the taper of which corresponds to that of the bores 9, 11 so that, when they are placed in the bottom of the recesses 6, 7 or in the bottom of semi-cylindrical channels receiving the rods 2 and 3, they do not project and are blocked in axial abutment by the presence of the rod.

Cavities 55 provided in the surface of each recess (FIG. 3) facilitate the supporting of a boring tool (not shown) providing a prior bore for the bore 9, 11.

Figure 5:
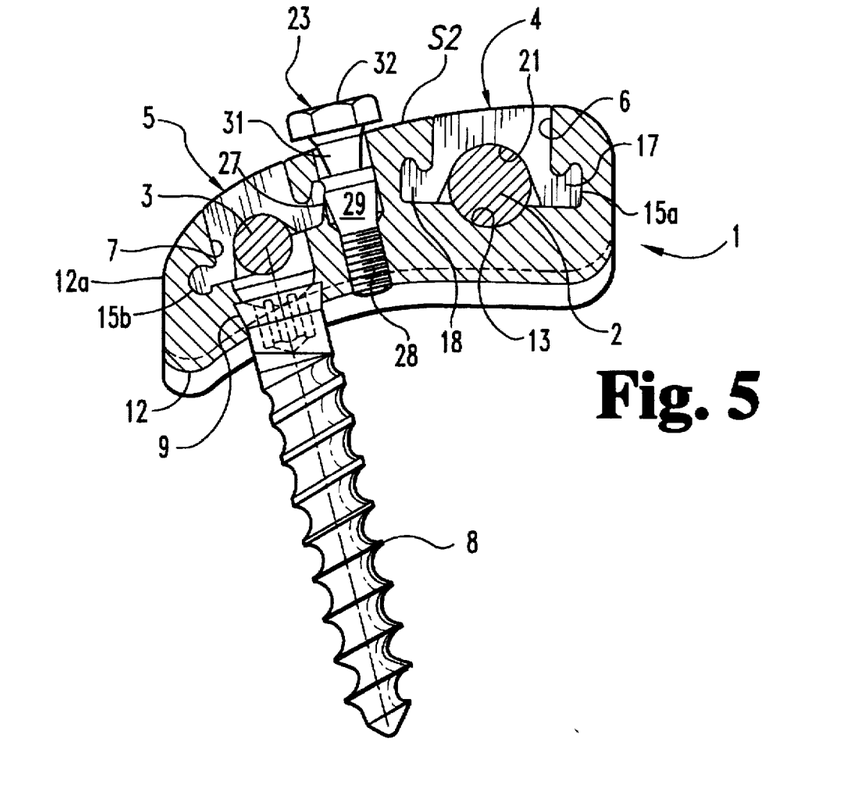
FIG. 5 is a cross-sectional view taken on line 5—5 of FIG. 4.
Figure 6:
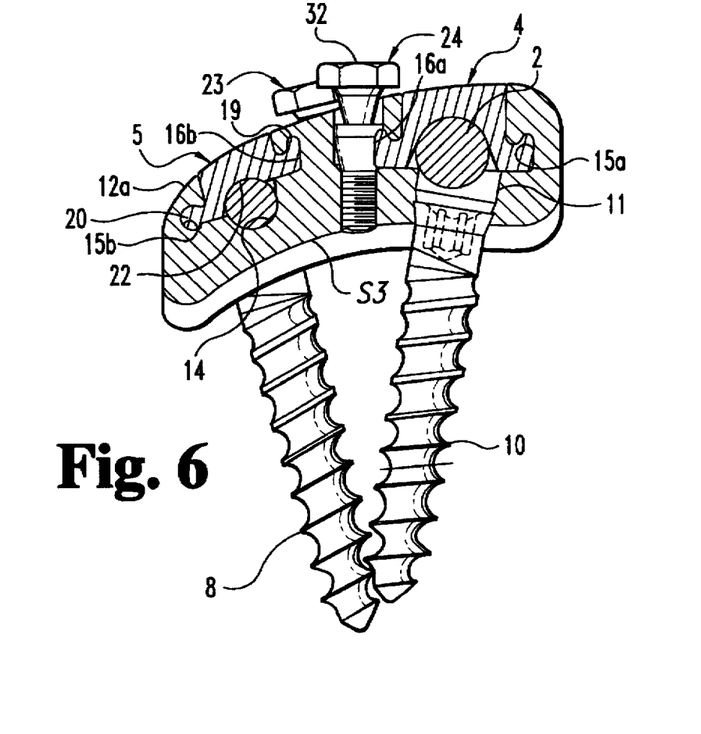
FIG. 6 is a cross-sectional view taken on line 6—6 of FIG. 4.
Figure 7:
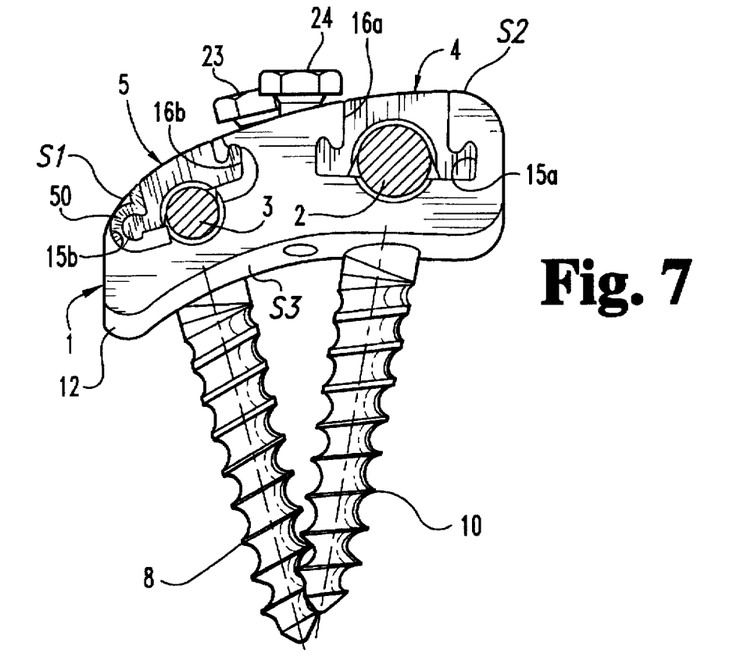
FIG. 7 is an elevational view of the instrumentation shown in FIGS. 4 to 6.
Figure 8:
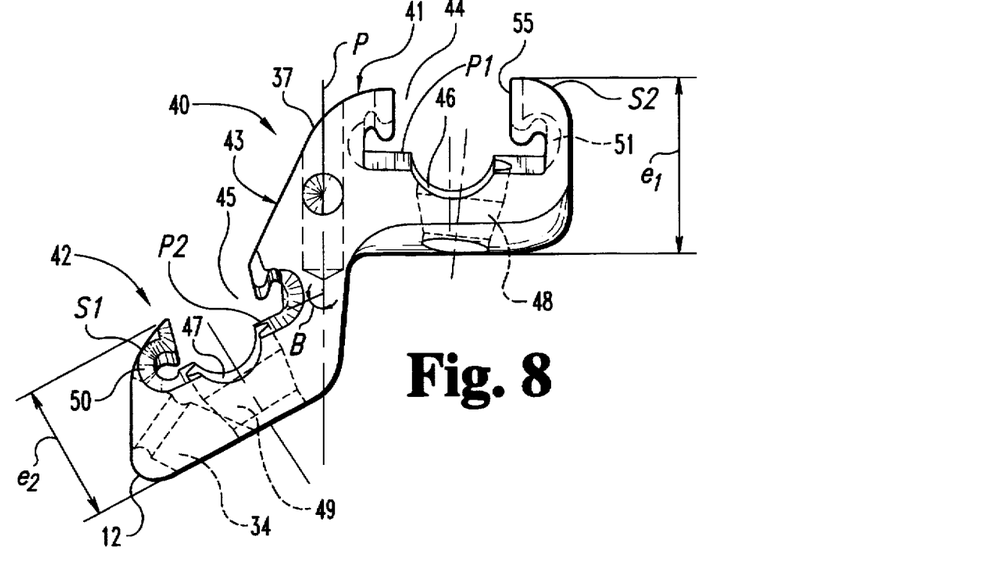
FIG. 8 is an elevational view of a second embodiment of the block of the instrumentation according to the invention.
Figure 9:
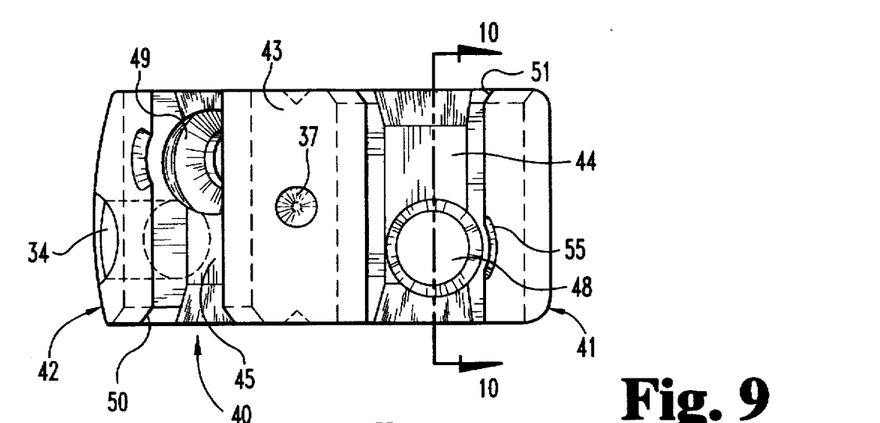
FIG. 9 is a top plan view of the block shown in FIG. 8.
Figure 10:
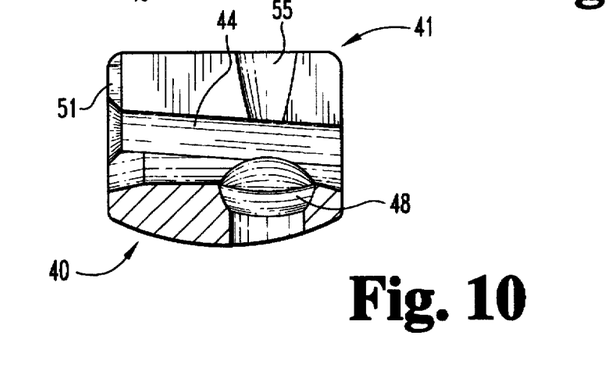
FIG. 10 is a half-elevational and half-sectional view taken on line 10—10 of FIG. 9.

Each block 1, 2 has, in the transverse direction from the anterior part toward the posterior part of the vertebral bodies on which they must be anchored by means of the screws 8, 10, a generally curved shape shown in particular in FIGS. 5 to 7 and corresponding to the antero-lateral anatomy of the vertebral bodies. Thus, this outer surface has a substantially convex shape from the anterior surface S1 to the posterior surface S2, while the interior surface S3, adapted to be applied against the vertebral body, is concave.

Each block 1, 2 has a substantially rectangular general shape of which the anterior region has a thickness less than that of the posterior region and the edges 12, 12a are rounded. Correspondingly, the radius of curvature of the anterior surface S1 is distinctly less than that of the posterior surface S2.

The upper surface (S2, S1) of each block is smooth owing to the fact that the surface of the slides 4, 5 are flush with the surrounding surface of the block, thereby avoiding any projection. The two recesses 6 and 7 extend in a direction parallel to each other and are each adapted to receive a portion of the respective rod 2, 3: the posterior rod 2 has a diameter distinctly larger than that of the rod 3 for a reason which will be explained hereinafter. The whole of the device must be disposed in most cases on the left side of the spine with the rod 2 in the posterior position.

Arranged in the bottom of each recess 6, 7 is a semi-cylindrical channel 13, 14 whose diameter corresponds to that of the respective rod 2, 3. Further, two lateral grooves 15a, 16a and 15b, 16b are formed in the sides of each recess 6, 7 in parallel relationship. These lateral grooves are adapted to receive corresponding lateral flanges 17, 18, 19, 20 of the respective slides 4 and 5. The flanges 17, 18, on one hand, and 19, 20, on the other, are arranged in a substantially different manner, as can be seen in FIGS. 5 to 7, owing to the dissymmetry between the posterior and anterior parts of each block 1. Consequently, the same is true of their corresponding grooves (15a, 16a, 15b, 16b).

The flanges 17, 18 and 19, 20 are inclined at a suitable angle A (FIG. 2) on the bottom of the recesses 6, 7 in the same way as their respective lateral grooves 15a . . . 16b which have for this purpose ramps of the same inclination A as the flanges 17 . . . 20. Thus the progressive insertion of each slide 4, 5 in the corresponding recess 6, 7 in the direction of the arrows (FIGS. 1 and 4) results in a progressive gripping of the flanges 17, 18 and 19, 20 in their grooves 15a, 16a . . . and finally the clamping of the slides in the recesses 6, 7. The inclinations of the flanges (17 . . . 20) are inverted on the slides 4 and 5 so that the latter are inserted in the recesses 6, 7 in opposite directions indicated by the arrows (FIGS. 1 and 4) to obtain a technical result which will be explained hereinafter. The angle of inclination A of the flanges 17, 18 and 19, 20 and of the ramps may be between about 2° and 6°.

The entry ends of the flanges (19 . . . 20) are advantageously machined in such manner as to have chamfers or rounded edges, such as 17a (FIG. 2). Correspondingly, the entry edges of the recesses 6, 7 also have chamfers not, shown in FIGS. 1 to 7 but shown in FIGS. 8 to 12 (50, 51). In cooperation with the chamfers 17a, these chamfers facilitate the insertion of the slides 4, 5 in their recesses 6, 7.

It should be noted that the semi-cylindrical channels 13, 14 are of course completed by corresponding channels 21, 22 provided in the slides 4, 5 (FIGS. 5 to 7).

Each block 1 can include complementary clamping means for each slide 4, 5. In the illustrated embodiment, these clamping means comprise, for each slide 4, 5, a respective screw 23, 24 which can be inserted in an opening 25, 26 provided in the central part of the block 1 between the recesses 6, 7. The opening 25 for the screw 23 communicates through a lateral passage 27 (FIG. 5) with the adjacent groove 16b of the lateral flange 19 of the slide 5. Likewise, the opening 27 of the passage between the opening 26 for the screw 24 and the groove 16a of the flange 18 of the slide 4 is shown in FIG. 5. Each screw 23, 24 has, from one end to the other, a screw threaded bone anchorage stem 28, a conical portion 29 which tapers toward the screw threaded stem 28, a fracture cone 31 which tapers toward the conical portion 29, and lastly a screwing head 32.

The end of the screw threaded portion 28 is rounded and is substantially flush with the interior surface S3 of the block 1. This screw threaded portion 28 is so dimensioned, as is the conical portion 29, that the latter bears against the adjacent flange 18, 19 of the respective slide 4, 5 by extending through the opening of the passage 27 (FIGS. 5 and 6).

Figure 13:
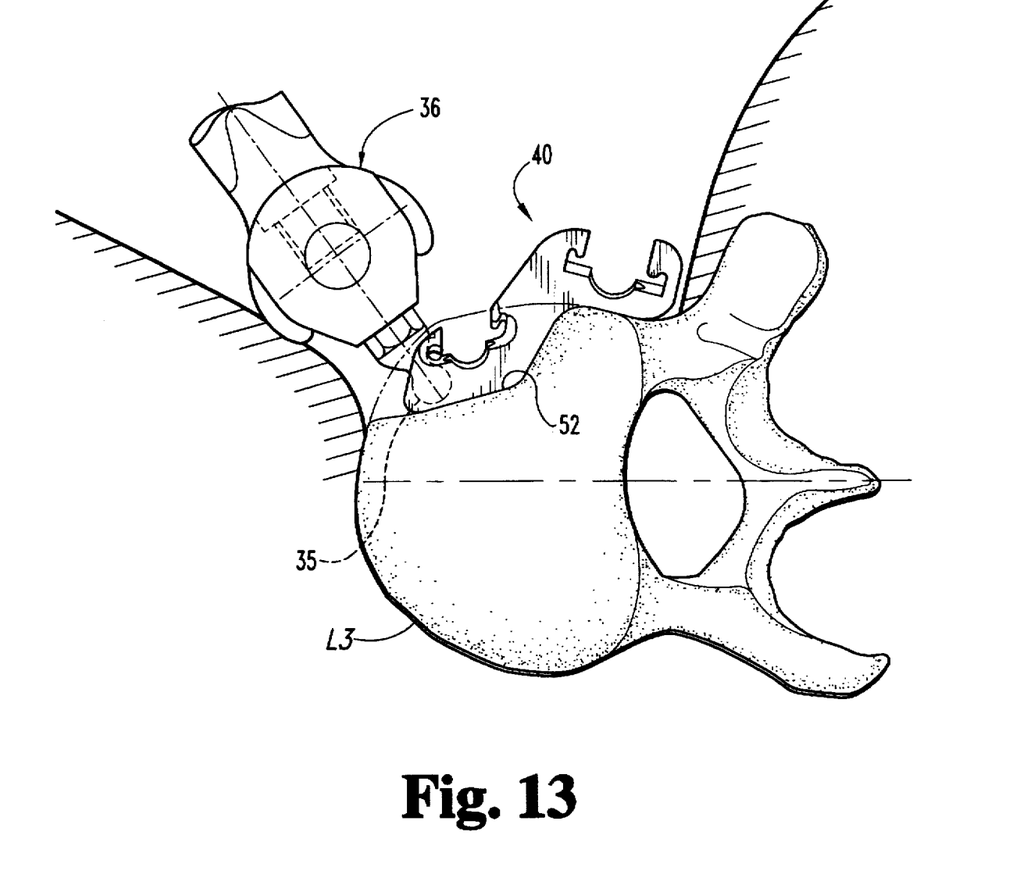
FIG. 13 is a top plan view of a vertebra, of a block according to the embodiment shown in FIGS. 8 to 12 applied to said vertebra, and a distraction-compression tool whose end is engaged in a lateral opening in the block provided for this purpose.

An aperture 34 is provided in the anterior part of each block in the surface S1 between the recess 7 and the rounded edge 12. This aperture 34 is adapted to receive the rounded head 35 of a distraction-compression tool 36 (FIG. 13) which is known per se and does not require description.

The implantation of the block 1 or "clip-block" requires the use of specific ancillary devices:

Ancillary device for mounting the slides 4 and 5: on each side of these slides, i.e. on the edges of their free ends, there is provided a notch which permits an effective and firm engagement of the ancillary device;

Ancillary device for mounting the block 1: an opening 37 provided in the central part of the block 1 (FIG. 1) facilitates the engagement;

Distraction ancillary device: the bore 34 in the anterior part of the blocks 1 permits the engagement of the distraction ancillary device 36 on either one of the clip-blocks 1.

The posterior rod 2 may have a diameter of 4 to 7 mm while the anterior rod 3 has a smaller diameter of 3 to 6 mm. This difference between the diameters is explained by the fact that it is on the posterior rod 2 that the main forces are exerted, in particular those due to derotation. On the other hand, the anterior rod 3 is subjected to smaller mechanical forces and may consequently have a smaller diameter. Further, this anterior rod 3 is the closest to the large blood vessels so that its reduced diameter increases the surgical safety of the instrumentation. However, this difference in diameter is not obligatory and the two rods 2 and 3 may possibly have the same diameter.

Figure 14:
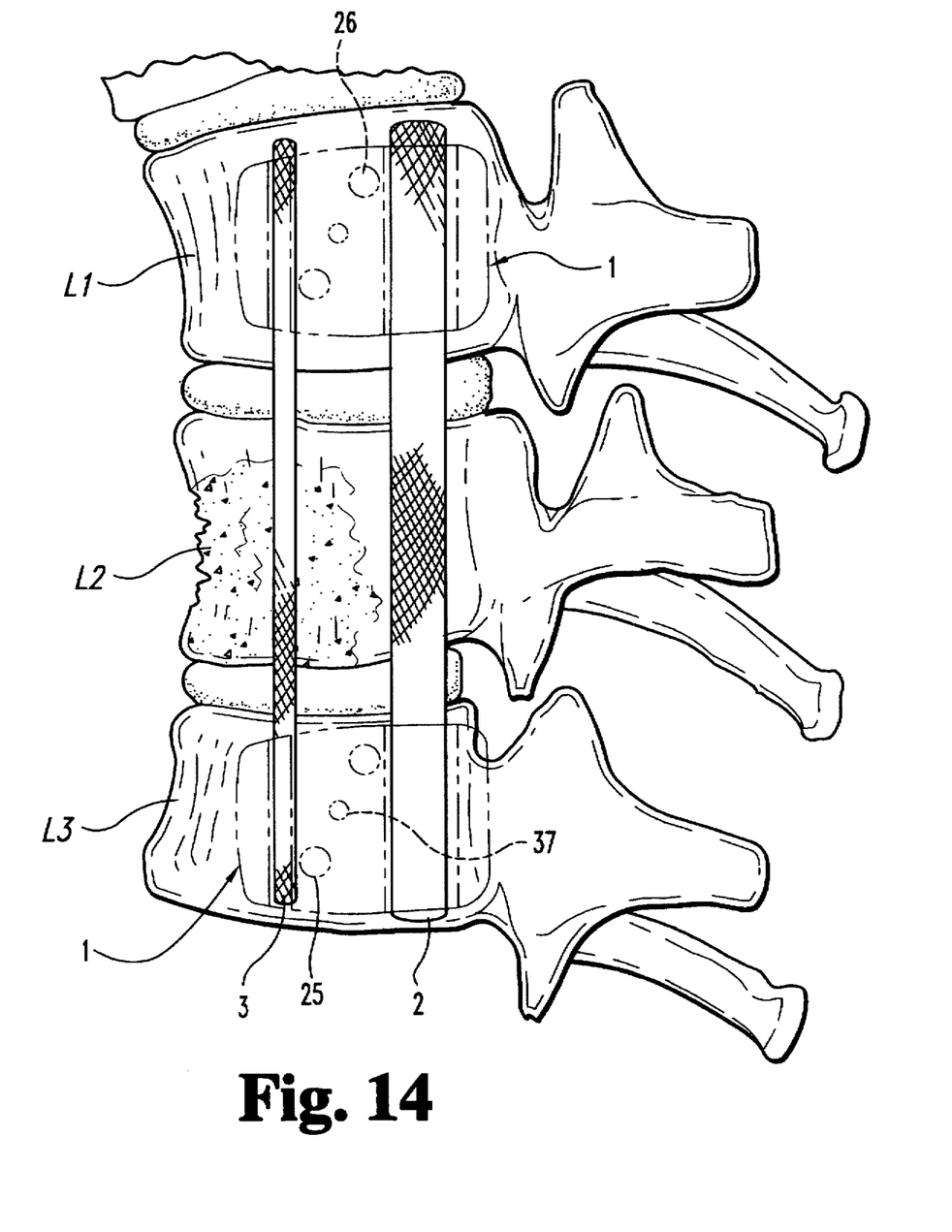
FIG. 14 is an elevational view of an instrumentation according to that shown in FIGS. 1 to 7, placed in position on a spinal segment having three vertebrae.

FIG. 14 shows an embodiment of the instrumentation according to the invention constituting a short arrangement extending along a vertebral segment of three vertebrae L3, L2, L1. The sequence of the mounting of the component parts of this instrumentation is the following:

A block 1 is placed on and then secured to the anterolateral side of the body of the vertebra L3 by means of vertebral screws 8, 10. Another block 1 is also placed in position and then secured in the same way to the body of the vertebra L1, the vertebra L2 being the vertebra to be treated.

A posterior rod 2, for example having a diameter of 6 mm, is placed in the posterior recesses 6 in the upper block and lower block. By means of a suitable ancillary device, the posterior slides 4 corresponding to the recesses 6 are installed on their respective inclined ramps 6a, 7a and are placed in contact with the upper side of the rod 2. This rod is thus trapped in the recesses 6 of the blocks but remains movable in translation and rotation under the action of outside forces. This is why the position of the slides on their clamping ramps, or intermediate position, must be such as to permit acting in complete safety on the rod without allowing the latter to escape from its recess. The slides are consequently not pushed to the end of their inclined ramps.

Such an intermediate position of the slides enables the surgeon to effect if necessary a derotation action on the vertebral column by revolving the posterior rod 2 about itself. Corresponding to this derotation is a new position of the rod 2 relative to the connecting recesses 6, this position being automatically obtained in accordance with the nature of the change brought about in the vertebral column by the derotation effect.

Then an anterior rod 3, for example having a diameter of 4 mm, of the same length as the posterior rod 2 in the embodiment shown in FIG. 14 (no slides are shown), is inserted in the anterior recesses 7 of the upper block and lower block. As for the rod 2 and the slides 4 of the recesses 6, the anterior slides 5 are placed on their respective inclined ramps in such manner as to maintain the rod 3 in a trapped position but sufficiently free to move in particular in translation. Their gripping action round the rod is therefore not complete as they are not pushed to the end of their inclined ramps.

Thus, depending on the nature of the pathology to be treated, an intervention involving distraction or compression of the vertebrae relative to one another may be performed by the surgeon by means of the ancillary device 36 or a like ancillary device the studs 35 of which are inserted in the bores 34 located in the anterior parts of the two blocks.

As soon as the desired distraction or compression is obtained, all the slides 4, 5 of the blocks are pushed right to the ends of their respective ramps and thus exert on the rods 2, 3 a progressively increasing gripping pressure which firmly clamps the rods in their respective recesses 6, 7 against rotation and translation.

As soon as the slides 4, 5 are fully clamped, the installation of the instrumentation is finished. Owing to the constitution of the blocks according to the invention, the rectangulation or framing effect of the appliance, similar to that achieved by a plate, is obtained without the addition of complementary parts such as transverse connection rods.

Lastly, in order to afford an additional safety in the clamping of the rods and slides in their recesses, the screws 23, 24 are inserted in the apertures 25, 26, tightened and then broken off in the region of their fracture cone provided for this purpose.

As concerns the constitution of the instrumentation according to the invention, it is important to notice the reliability of the device, in particular in the anchorage of the blocks 1 to the vertebrae. The anchorage screws 8, 10 are indeed intentionally placed at the bottom of the recesses and advantageously possess a conical head (FIGS. 5 and 6) corresponding to the taper of the bores 9, 11 so that the head does not assume a projecting position in the semi-cylindrical channels 13, 14 receiving the rods 2, 3.

When the instrumentation is definitively installed, i.e. after completely closing the slides 4, 5, the anchorage screws 8, 10 are also clamped and can in no way, under the multiple effects of the movements of the body of the patient, become detached from the vertebral column in which they are inserted. Their axial displacement is rendered impossible so that, in the event of a possible fracture in any region of its length, the two screw portions are held fast and nonetheless maintain the block.

Figure 4:
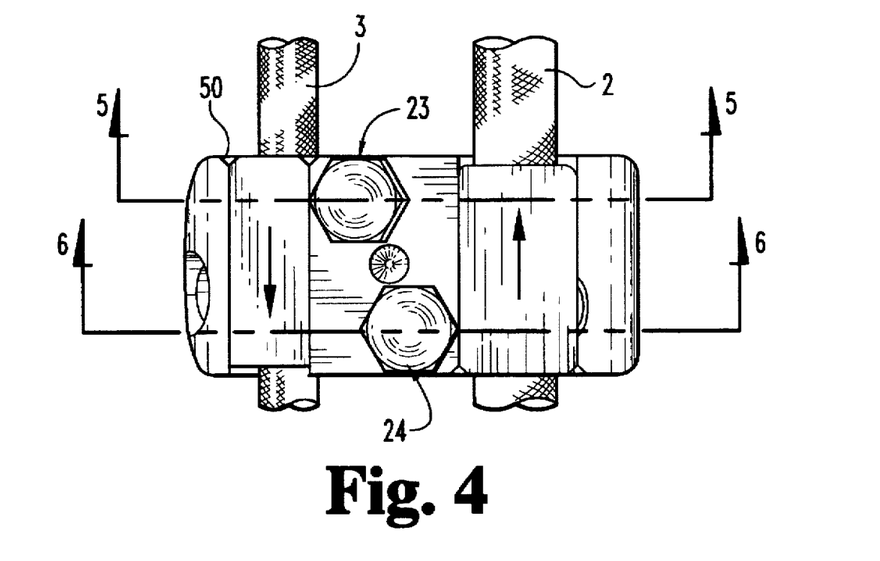
FIG. 4 is a partial top plan view of the instrumentation shown in FIGS. 1 to 3.
Figure 11:
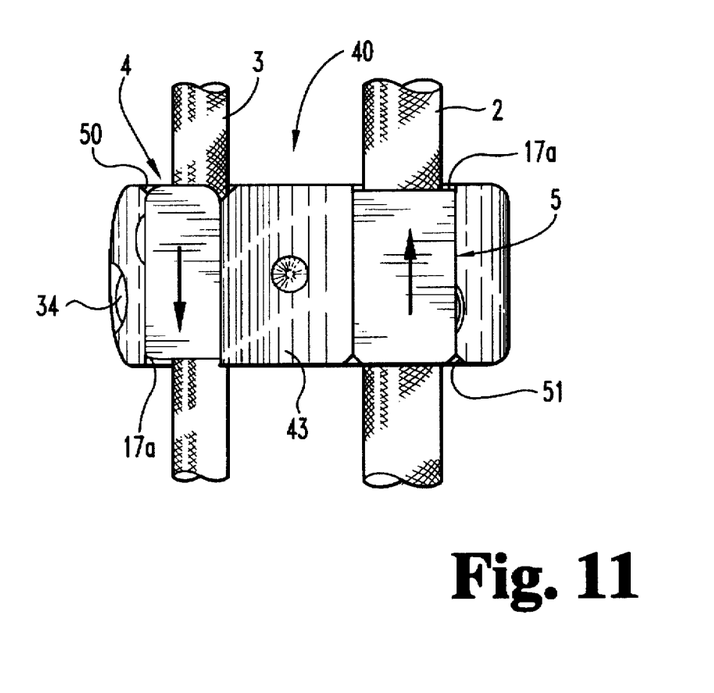
FIG. 11 is a partial top plan view of an instrumentation according to the embodiment shown in FIGS. 8 to 10.
Figure 12:
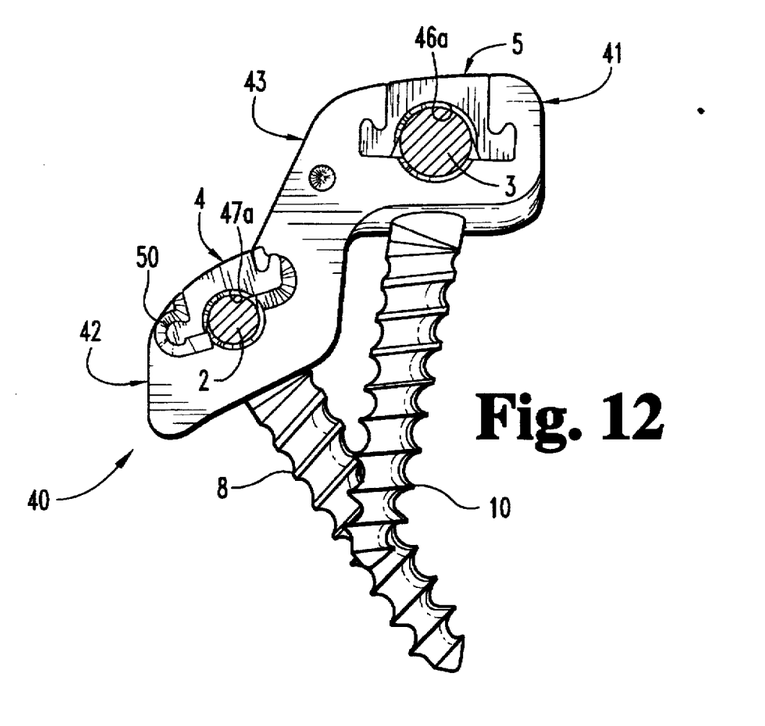
FIG. 12 is an elevational view of the block and the screws shown in FIG. 11, the rods being shown in cross-section.

Note also that the slides of each rod are inserted in the same axial direction, but for each of the rods the direction of insertion of the slides is inverted, as shown by the arrows in FIGS. 1, 4 and 11 engraved on the upper surface of the slides 4, 5. In this way, as the inclined ramps of the recesses 6, 7 are arranged to permit such an inverted insertion of the slides of each block 1, after the slides are clamped in position, all the forces exerted by the multiple movements of the patient on one of the rods which tend to untighten the assembly are taken by the other rod in the opposite direction for exerting gripping forces. They are in this way neutralized, this arrangement therefore considerably increasing the reliability of the whole of the instrumentation.

The instrumentation according to the invention has still further technical advantages:

First of all, the rectangular structure obtained by the assembly of two clip-blocks 1 with their slides 4, 5 and the two rods 2, 3, constitutes a device for the fixation and the rectangulation of the assembly providing an improved stabilization. In instrumentations of the prior art having rods, it was necessary for the two rods to be definitively fixed for placing in position a transverse connection device (rectangulation). Owing to the present invention, the rectangulation of the device is automatically obtained by the mounting of the anterior consolidation rod 3.

Strength for resisting physiological loads over a period of time, avoiding an excessively long fusion, permitting a rapid mobilization of the patient with no external immobilization, and avoiding an additional fixation by the posterior approach requiring a second surgical intervention.

Possibility of an instrumental correction in the three dimensions so as to restore the spinal profile (by a relative compression or distraction of the vertebrae), possibility of a complete correction of deviations, possibility of a complete correction of the vertebral rotation and of the gibbosity of the column for the reequilibrium of the latter.

Small volume not only as concerns thickness so as to avoid contact with the large vessels, but also as concerns the amount of metal employed. For example, this thickness should not exceed 11 mm in the posterior third of the vertebral body and 9 mm in the middle third. This avoids any interference with the consolidation of the bone graft.

Simplicity of positioning by the surgeon, owing to the small number of component parts making up the instrumentation. This reduces the number of ancillary devices required and consequently the overall cost of the instrumentation.

Facility and rapidity of implantation by the surgeon who, for the reasons mentioned before, must as far as possible reduce any risk of neurological injury.

Flexibility of utilization permitting the instrumentation to be not only universal in its spinal application but also to be adapted to all levels of the vertebral column, in particular from T4 to L5, with implants of different sizes and different shapes.

Considerable safety of utilization owing to the fact, in addition to the foregoing features, that each anchorage screw 8, 10, once inserted in its bore 9, rests therein in a completely trapped manner. Indeed, the cylindrical rod 2, 3 is clamped on the head of the screw 8, 10 by the corresponding slide 5, 4 after the complete closure of the latter. Consequently, the screw is completely blocked in the axial direction and, if a transverse fracture of its screw threaded portion occurs, its consequences on the patient would be slight if not practically nil.

The force exerted for completely closing the slides 4, 5 is sufficiently high to prevent the accidental opening of the latter owing to the action of each longitudinal flange (17 ... 20) and its chamfered end 17a which permits a privileged insertion in one direction rather than in the other (see FIGS. 1 and 4). This is the reason for the provision of arrows on the surface of the slides 4 and 5 which indicate the direction of insertion of each slide. This arrangement is made necessary by the slope of the sliding and gripping longitudinal flanges.

The upper surface of each clip-block 1 is completely smooth, in particular in its most rounded lateral part S1 corresponding to the anterior positioning on the vertebrae. The upper surface of the slides 4, 5 which is also smooth is flush with the surfaces S1, S2 of the lateral parts and of the central part of the block 1, so that no particular element projects. This is a notable advantage of the clip-block provided by the invention.

The screws 23, 24 clamping the slides 4 and 5 afford additional safety to the instrumentation by the tightening of their conical portions 29 on the flanges 18 and 19 of the slides 4, 5. It concerns an additional safety means with respect to the clamping of the slides 4, 5 on the rods C–D 2 and 3, since the clamping is in any case assured by the clamping of the slides on the rods. The screws 23, 24 therefore only have an additional subsidiary effect. In order to avoid projecting from the surface of the block 1, each screw 23, 24 is broken off in its upper part after tightening on the block, with the aid of the fracture conical portion 31. This fracture therefore occurs at the junction between the fracture conical portions 31 and the tightening conical portions 29, in the weakest region. Thus each screw 23, 24 is practically hidden in the block 1 since the fracture plane is approximately at a distance of 2 to 3 mm from the surface S2 of the block 1.

In the second embodiment of the invention shown in FIGS. 8 to 13, each block 40 has a generally bent shape so as to have an approximately S-shaped cross-section. The two halves 41 and 42 of the block 40 respectively constitute its posterior and anterior parts, the posterior part 41 having a thickness e1 greater than the thickness e2 of the anterior part 42. The two parts 41, 42 are interconnected by a central part 43 which extends in a general direction P substantially perpendicular to the plane P1 of the bottom of the recess 44 of the posterior part 41. On the other hand, the general direction P in which the central part 43 extends makes an angle B of less than 90° with the plane P2 of one of the sides of the bottom of the recess 45 of the anterior part 42. As in the blocks 1, semi-cylindrical channels 46, 47 are provided in the bottom of the respective recesses 44, 45 and complementary channels 46a, 47a in the slides 4, 5, the diameters of said channels corresponding to those of the rods 2 and 3. Bores 48, 49 are provided in the bottom of the channels 46, 47 for receiving anchorage screws 10 and 8 respectively. Note that in FIGS. 8 and 9 the entry chamfers 50, 51 of the recesses 44 and 45 facilitate the insertion of the corresponding slides 4, 5. Further, the arrangement of the block 40 is similar to that of the block 1, the same reference numerals being used for the corresponding parts in both cases.

When the component parts of this instrumentation have been assembled (FIGS. 11 and 12), the anchorage screws 10 and 8 respectively extend through the posterior part 41 and anterior part 42 and make an angle therebetween on the order of 35° to 40°. The anterior part 42 is then placed in a vertebral recess 52 (FIG. 13) produced by the surgeon and opening onto the anterior part of the vertebra, for example L3 or L1. Thus the anterior part 42 of the clip-block 40 is inserted in the vertebral region. The angle between the posterior part 41 and anterior part 42 (corresponding to the angle between the two planes P1 and P2) affords additional safety to the surgeon bearing in mind the proximity of the large vessels in the anterior approach.

The edge 12 of the anterior part S1, which is slightly rounded in the transverse direction as already mentioned, may have a radius of curvature of about 15 mm. This specific shape corresponds to the mean estimation of the value of the concavity of the vertebra in the region of the implantation of the block 1, 40 on the latter. This disposition contributes to the obtainment of the desired stability of the whole of the instrumentation owing to the fact that there is in this way an improved distribution of the forces exerted by the concerned faces in contact.

As explained before, the directions of insertion of the slides 4 and 5 are opposite so that over a period of time, when the patient resumes his activity, no loosening of the slides can occur; Indeed, the forces which tend to loosen the slide or slides 4 clamping the posterior rod 2 (which is used for the derotation), can be opposed or balanced by the forces tending to loosen the slide or slides 5 clamping the anterior rod 2. Experience has shown that it is desirable to clamp the slides 4 on the posterior rod 2 in the upward direction while the clamping of the other rod 3 then occurs in the downward direction.

Such an assembly has an excellent mechanical behaviour. In strength tests with a static and dynamic testing machine, employing the maximum forces normally produced by the human body, it was not possible to detect a loss of connection.

It must be understood that the scope of the invention is not intended to be limited to the two described embodiments since many alternative embodiments may be envisaged. For vertebral segments longer than that illustrated in FIG. 14, the instrumentation may have the required number of clip-blocks 1, for example three or four.

Likewise, it could be necessary that, as opposed to the embodiment shown in FIG. 14, the two rods 2 and 3 be exceptionally different, for example that the posterior rod 2 extend beyond the anterior rod 3. In this case, the rods may be fixed as previously described, and the extending portion of the rod may be fixed by at least one clip-block according to the invention but defining a single recess 6 or 7. This block is then fixed so as to maintain the additional length of this rod, the recess for receiving the other rod being unnecessary.

The additional means for clamping the slides 4, 5 constituted by the pairs of screws 23, 24 may comprise only a single screw per block 1, which may be inserted in a central aperture in the block. This aperture and the screw then have a diameter which is sufficient to ensure that the aperture communicates through lateral passages with the adjacent grooves (16a, 16b) of the lateral flanges 18, 19 of the slides 4, 5. The screw is provided with a conical portion 29 positioned to engage in said lateral passages and come to bear against the flanges of the slides so as to reinforce their clamping in their recesses.

In this case, additionally, the aperture 34 may be advantageously eliminated, it being possible to carry out the distraction-compression operation by inserting the head of the ancillary device 36 in the central aperture of the screw.

What is claimed is:

1. Spinal osteosynthesis instrumentation for an anterior approach, said instrumentation comprising:
   two elongated rods;
   at least two blocks for transversely interconnecting said rods, said blocks defining openings for receiving said rods therein in such manner that said rods are axially slidable and revolvable about themselves in said blocks;
   means slidably disposed within said blocks and bearing against said rods for clamping said rods against rotation and translation relative to said blocks; and
   wherein each block has an anterior part and a posterior part and a generally curved shape in a transverse direction from said anterior part to said posterior part corresponding to the antero-lateral anatomy of vertebral bodies, said block defining a concave interior surface configured to contact a vertebral body and a convex exterior surface.

2. Instrumentation according to claim 1 wherein said anterior part has a thickness less than the thickness of said posterior part and has a rounded edge.

3. Instrumentation according to claim 1, wherein each block defines two recesses each receiving a respective rod; and
   said means for clamping includes a slide for each of said recesses, each slide being longitudinally slidably mounted in the respective longitudinal recess and becoming clamped on the respective rod at the end of the travel of said slide along the respective recess.

4. Instrumentation according to claim 3, wherein each slide is provided with inclined lateral flanges, complementary lateral grooves are provided in the respective recess, said inclined lateral flanges being engageable in said complementary lateral grooves, inclined clamping ramps are provided in said grooves, said flanges being cooperative with said clamping ramps, said ramps having an angle of inclination of substantially 2° to 6° relative to the axis of the respective rod.

5. Instrumentation according to claim 4, wherein each flange of each slide has an end which is the first to enter the respective recess and is chamfered and said respective recesses has an entrance which is chamfered whereby the insertion of said slides in said recesses is guided.

6. Instrumentation according to claim 5, wherein each slide bears an indicia indicating a direction of insertion of said slide into a respective longitudinal recess so that said end first enters the recess.

7. Instrumentation according to claim 5, wherein said block bears indicia indicating a direction of insertion of each slide into a respective longitudinal recess so that said end of each slide first enters the respective recess.

8. Instrumentation according to claim 4, wherein the inclinations of said lateral flanges of said slides and the inclinations of the associated clamping ramps are inverted between the two slides of each block.

9. Instrumentation according to claim 4, wherein the inclinations of said ramps and flanges of said slides are oriented in the same direction for the slides of tile same rod and in the opposite direction for the ramps and flanges of tile slides of the other rod.

10. Instrumentation according to claim 3, comprising semi-cylindrical channels forming seats for said rods provided in the bottom of said recesses of said blocks and in said slides.

11. Instrumentation according to claim 3, wherein each slide has a surface which is flush with an outer convex surface of the respective block so that said outer convex surface and said surface of each slide are together smooth and devoid of any projection.

12. Instrumentation according to claim 11, wherein each block comprises complementary clamping means for the respective slide.

13. Instrumentation according to claim 12, wherein said complementary clamping means comprise, for each slide, a screw insertable in an opening provided in the central part of the respective block between said recesses, said opening communicating through a lateral passage with the adjacent groove of a lateral flange of said slide, and said screw being provided with a conical portion positioned to engage in said lateral passage and come to bear against said flange of said slide to reinforce the clamping thereof in said groove.

14. Instrumentation according to claim 13, wherein said clamping screw comprises, from one end to the other thereof, a screw threaded anchoring stem, a conical portion for clamping said slide which tapers toward said screw threaded stem, a fracture conical portion which tapers toward said clamping conical portion, and a screwing head.

15. Instrumentation according to claim 12, wherein said complementary clamping means comprise a central aperture in each block, a screw insertable in said central aperture, said aperture and said screw having a sufficient diameter to enable said aperture to communicate through lateral passages with the adjacent grooves in said lateral flanges of the respective slide, and said screw is provided with a conical portion positioned to be engaged in said lateral passages and come to bear against said flanges of the slide and reinforce the clamping thereof in the respective groove.

16. Instrumentation according to claim 3, further comprising a cavity in a wall of each recess configured to receive a boring tool therethrough for boring in the vertebral body for inserting an anchorage screw In the vertebral body.

17. Instrumentation according to claim 1, wherein one rod is an anterior rod and has a diameter less than the diameter of the other rod which is a posterior rod.

18. Instrumentation, according to claim 1, comprising an opening in an anterior part of each block for receiving a distraction-compression tool.

19. Spinal osteosynthesis instrumentation for an anterior approach, said instrumentation comprising:

two elongated rods;

at least two blocks for transversely interconnecting said rods, said blocks defining openings for receiving said rods therein in such manner that said rods are axially slidable and revolvable about themselves in said blocks;

means slidably disposed within said blocks and bearing against said rods for clamping said rods against rotation and translation relative to said blocks;

a pair of anchorage screws for each of said blocks; and wherein each block defines two recesses each receiving respective one of said rods and a pair of bores each intersecting a corresponding one of said recesses, said means for clamping includes a slide for each of said recesses, each slide being longitudinally slidably mounted in the respective longitudinal recess and becoming clamped on the respective rod at the end of the travel of said slide along the respective recess, and said pair of anchorage screws each being inserted through a corresponding one of said pair of bores for each of said blocks.

20. Instrumentation according to claim 19, wherein said pair of anchorage screws are each supported in a respective one of said pair of bores to subtend an angle between said pair of screws for each of said blocks, said angle being substantially 25°.

21. Instrumentation according to claim 19, comprising semi-cylindrical channels forming seats for said rods in said recesses of said blocks and in said slides, each bore opening onto the respective semi-cylindrical channel receiving the respective rod so that each bone anchorage element is trapped in its bore when said respective rod is clamped in position by a complete engagement of the respective slide in the respective recess.

22. Instrumentation according to claim 19, wherein one of said rods has a first diameter and the other of said rods has a second diameter less than said first diameter.

23. Spinal osteosynthesis instrumentation for an anterior approach, said instrumentation comprising:

two elongated rods;

at least two blocks for transversely interconnecting said rods, said blocks defining openings for receiving said rods therein in such manner that said rods are axially slidable and revolvable about themselves in said blocks;

means slidably disposed within said blocks and bearing against said rods for clamping said rods against rotation and translation relative to said blocks; and wherein said block is curved in such manner as to have in cross-section a substantially S-shape having one half which constitutes an anterior part and a second half constituting a posterior part, said anterior part having a thickness which is less than the thickness of said posterior part and being capable of being inserted in a cavity provided for this purpose in the vertebral body.

24. Instrumentation according to claim 23, wherein one of said rods has a first diameter and the other of said rods has a second diameter less than said first diameter.

25. Instrumentation of claim 23, wherein each of said recesses for each of said blocks defines a bore therethrough configured to received an anchorage screw.

26. Spinal osteosynthesis instrumentation for engaging at least two elongated rods to the anterior aspect of the spine, comprising:

a block having a longitudinal length and defining two longitudinal recesses along said longitudinal length, each of said recesses configured to receive a rod therein and defining a longitudinal axis;

means for clamping the rods within each of said recesses, said means including a slide disposed in each of said recesses, said slide being slidably mounted in a respective longitudinal recess for travel from one end of said recess toward an opposite end of said recess, said slide clamping a rod within said respective longitudinal recess along the travel of said slide; and wherein said block is formed from a unitary piece to define a fixed transverse distance separating said two recesses from each other.

27. Spinal osteosynthesis instrumentation according to claim 26, wherein:

said block defines an opening between said two recesses, said opening communicating through a lateral passage with at least one of said recesses; and said instrumentation further includes a screw engageable within said opening and having a conical portion configured to extend through said lateral passage when said screw is engaged within said opening, whereby said conical portion bears against said slide disposed within said at least one of said recesses.

28. Instrumentation of claim 26, wherein one of said recesses is sized to receive one of the rods having a first diameter and other of said recesses is differently sized to receive another of the rods having a second diameter, said second diameter being less than said first diameter.

29. Spinal osteosynthesis instrumentation for engaging at least two elongated rods to the anterior aspect of the spine, comprising:

a block having a longitudinal length and defining two longitudinal recesses along said longitudinal length, each of said recesses configured to receive a rod therein and defining a longitudinal axis;

means for clamping the rods within each of said recesses, said means including a slide disposed in each of said recesses, said slide being slidably mounted in a respective longitudinal recess for travel from one end of said recess toward an opposite end of said recess, said slide clamping a rod within said respective longitudinal recess along the travel of said slide; and wherein said block defines at least one lateral groove along each of said elongated recesses and each of said slides includes at least one lateral flange complementary with and slidable within a corresponding lateral groove.

30. Spinal osteosynthesis instrumentation according to claim 29, wherein said at least one lateral groove along each of said recesses defines a clamping ramp inclined relative to said longitudinal axis of said recess, said lateral flange of each of said slides being cooperative with said clamping ramp to clamp said lateral flange within said recess along the travel of said slide.

31. Spinal osteosynthesis instrumentation according to claim 30, wherein said clamping ramp defined in each of said recesses is inclined at substantially 2°–6° relative to said longitudinal axis of said recess.

32. Instrumentation of claim 29, wherein one of said recesses is sized to receive one of the rods having a first diameter and other of said recesses is differently sized to receive another of the rods having a second diameter, said second diameter being less than said first diameter.

33. Spinal osteosynthesis instrumentation for an anterior approach, comprising:

a first elongated rod;

a second elongated rod having a diameter less than the diameter of said first elongated rod;

a block for transversely connecting said first and second rods adjacent the spine, said block defining a first elongated recess configured to receive said first rod therein and a second elongated recess configured to receive said second rod therein; and means for clamping said first and second rod within said first and second recess, respectively, against rotation and translation relative to said block.

34. Spinal osteosynthesis instrumentation for engaging the anterior aspect of a patient's spine, comprising:

a first spinal rod configured for fixation along the patient's spine;

a second spinal rod configured for fixation along the patient's spine adjacent to said first rod;

a block transversely interconnecting said first and second spinal rods, said block defining a first elongated recess configured to receive said first rod and a second elongated recess configured to receive said second rod;

a first slide configured to slidingly engage said first recess to clamp said first rod between said first slide and said block when said first rod is received in said first recess; and a second slide configured to slidingly engage said second recess to clamp said second rod between said second slide and said block when said second rod is received in said second recess.

35. Spinal osteosynthesis instrumentation according to claim 34, wherein:

said block defines a first lateral groove along said first recess and a second lateral groove along said second recess;

said first slide includes a first flange for slidingly engaging said first groove; and said second slide includes a second flange for slidingly engaging said second groove.

36. Spinal osteosynthesis instrumentation according to claim 35, wherein:

said first lateral groove defines a first clamping ramp inclined relative to a longitudinal axis of said block, said first lateral flange being cooperative with said first clamping ramp to clamp said first lateral flange within said first recess; and said second lateral groove defines a second clamping ramp inclined relative to said axis, said second lateral flange being cooperative with said second clamping ramp to clamp said second lateral flange within said second recess.

37. Spinal osteosynthesis instrumentation according to claim 34, wherein said first rod has a smaller diameter than said second rod.

38. Spinal osteosynthesis instrumentation according to claim 34, wherein said block defines a first bore intersecting said first recess and further comprising a first anchorage screw inserted through said first bore.

39. Spinal osteosynthesis instrumentation according to claim 38, wherein said block defines a second bore intersecting said second recess and further comprising a second anchorage screw inserted through said second bore, said first and second anchorage screws subtending an angle therebetween of about 25°.

40. Spinal osteosynthesis instrumentation according to claim 34, wherein:

said block defines an opening between said first and second recesses, said opening communicating through a lateral passage with at least one of said first and second recesses; and said instrumentation further includes a screw engageable within said opening and having a conical portion configured to extend through said lateral passage when said screw is engaged within said opening, whereby said conical portion bears against at least one of said first and second slides when disposed within a corresponding one of said first and second recesses.

* * * * *